Figure 1:
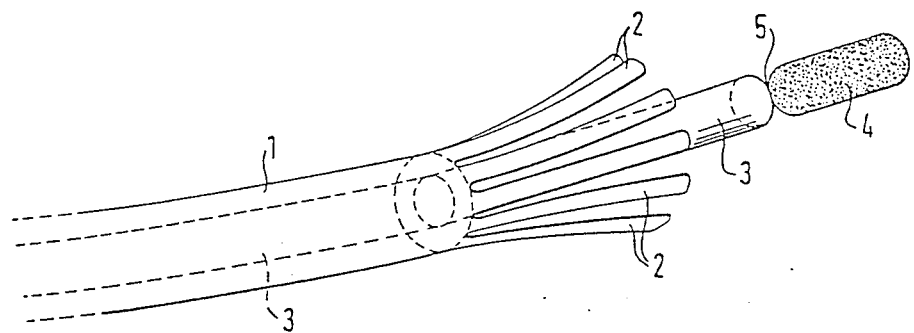

United States Patent [19]

Reinmüller

[11] Patent Number: 4,960,415
[45] Date of Patent: Oct. 2, 1990

[54] DEVICE FOR INSERTING IN WOUNDS AND WOUND CAVITIES

[75] Inventor: Johannes Reinmüller, Ulm, Fed. Rep. of Germany

[73] Assignee: Merck Patent GmbH, Darmstadt, Fed. Rep. of Germany

[21] Appl. No.: 274,647

[22] Filed: Nov. 18, 1988

Related U.S. Application Data

[63] Continuation of Ser. No. 878,842, filed as PCT GB85/00390 on Sep. 30, 1985, published as WO86/01415 on Mar. 13, 1986, abandoned.

[30] Foreign Application Priority Data

Sep. 6, 1984 [DE] Fed. Rep. of Germany ....... 3432825
Feb. 22, 1985 [DE] Fed. Rep. of Germany ....... 3506288

[51] Int. Cl.$^5$ ......................... A61F 5/46; A61M 25/00
[52] U.S. Cl. ............................. 604/890.1; 604/891.1; 604/265
[58] Field of Search ............................. 604/890.1–892.1, 604/265, 285, 93, 29

[56] References Cited

U.S. PATENT DOCUMENTS

| 3,279,996 | 10/1966 | Long et al. | |
|---|---|---|---|
| 3,406,691 | 10/1988 | Kettenback | 604/93 |
| 3,815,608 | 6/1974 | Spinosa et al. | 604/103 |
| 3,948,254 | 4/1976 | Zaffaroni | |
| 4,144,317 | 3/1979 | Higuchi et al. | |
| 4,344,431 | 8/1982 | Yolles | 604/891 |
| 4,468,216 | 8/1984 | Muto | |
| 4,483,688 | 11/1984 | Akiyama | 604/265 |
| 4,515,593 | 5/1985 | Norton | 604/265 |
| 4,587,268 | 5/1986 | Pfirrmann | 514/774 |
| 4,603,152 | 7/1986 | Laurin et al. | 604/265 |
| 4,604,391 | 8/1986 | Pfirrmann | 514/222 |
| 4,692,153 | 9/1987 | Berlin et al. | 604/93 |

FOREIGN PATENT DOCUMENTS 0048558 3/1982 European Pat. Off. .
3217109 11/1983 Fed. Rep. of Germany .

Primary Examiner—John D. Yasko
Assistant Examiner—Anthony Gutowski
Attorney, Agent, or Firm—Felfe & Lynch

[57] ABSTRACT

A device for inserting in wounds and wound cavities is described consisting of a container containing a pharmaceutical active substance, the walls of this container consisting at least partly of a membrane, preferably a semi-permeable membrane, which allows the active substance to escape into the wound area. The container is, more preferably, a dialysis tube. In order to drain off wound secretions, the container containing the pharmaceutically active substance, particularly taurolidine, is conveniently connected to a drainage tube. Preferably, a drainage tube is used in which the end which leads into the wound is split into filaments.

14 Claims, 1 Drawing Sheet

DEVICE FOR INSERTING IN WOUNDS AND WOUND CAVITIES

This application is a continuation, of application Ser. No. 878,848, filed as PCT GB85/00390 on Sep. 30, 1985, published as WO86/01415 on Mar. 13, 1986, now abandoned.

The invention relates to a device for inserting in wounds and wound cavities in humans and animals.

In the event of injury or after surgical intervention it may be appropriate or necessary to threat the wound or wound cavity with substances having an anti-bacterial and/or anti-toxic activity. This is particularly important if the wound is infected with bacteria and/or if bone tissue is affected by the infection. The treatment of osteitis or osteomyelitis is a problem to which there has not hitherto been a satisfactory solution. It is already known to implant bactericides in the bones. It is known, for example, to shape bone cement consisting of polymethylmethacrylate (PMMA) into bead-like pellets which contain a bactericide (e.g. rivofazin). A number of these pellets are strung together with wire like a string of beads and implanted in the diseased bone so that the string or cord, possible together with the outermost bead, projects and after some time the entire implant can be pulled out by means of this bead. However, the effectivess of this implant leaves much to be desired.

Taurolidine (4,4' methlyen-bis(tetrahydro-2H-1,2,4-thiadiazin-1,1-dioxide)) has proved a particularly effective bactericidal substance. The bactericidal activity appears to be based on the destruction of the bacterial cell wall by the transfer of methylol groups whilst at the same time the lipopolysaccharides of the bacterial endotoxins and the proteins of the bacterial exotosins are denatured and detoxified. In this way, toxic shock with the possibility of severe organ damage after anti-bacterial treatment can be avoided (cf. see steinbach-Lebbin et al, Drug Research 32 (II), No. 12 (1982), 1542 to 1546). Taurolidine has relatively low solubility in water ( about 1–2% ). In view of its very good batericidal properties (stronger than many antibiotics) and other properties ( avoidance of bacterial resistance, local irritation or other undersirable side effects), attempts have been made to use solutions of taurolidine as bone rinses to combact and treat osteomyelitis. The activity is, however, of extremely limited duration.

The present invention relates to a device for inserting in wounds and wound cavities which consists of a container containing a pharmaceutical active substance or which contains such a container, the walls of which consist at least partly of a membrane which enables active subtance to escape into the wound area.

The term "wound" for the purpose of this invention relates to wounds produced by trauma and/or surgical intervention but excludes incisions made solely for the implantation of a device of the type according to the invention containing an existing pharmacutically active substance as distinct from a precursor therefor.

The term "wound cavities" for the purposes of this invention relates not only to artifically produced body cavities i.e. those produced by trauma or operation, but also natural body cavities or hollow organs, e.g. the thoracic cavity, abdominal cavity or the bladder, which may become wound cavities as the result of being opened up in an operation.

With the pharmaceutical container according to the invention it is possible to avoid the problems which arise in connection with wound treatment, particular the treatment of osteomyelitis or purulent peritonitis, such as limited duration of activity. The pharmaceutical composition located in the container according to the invention is released through the membrane gradually and in constant quantities per unit of time, depending in part on its solubility. In this way, the substances can develop their activity in a controlled manner spread over a longer period. The pharmaceutical container according to the invention preferably contains pharmaceutical active subtances having an anti-bacterial and/or anti-toxic activity, such as antibiotics, anti-phlogistics, hormones or corticosteriods, particularly with a view to use in the treatment of wounds and osteomyelitis, whilst, depending on the envisaged application, it is also possible to use mixtures of two or more active subtances with identical, overlapping or different spectra of activity, e.g. two or more compounds of different solubility, which provide an additional means of controlling the release per unit of time and hence the duration of activity, or a combination of taurolidine and one or more antibiotics.

The pharmaceutically active substance taurolidine is particularly used in view of the intended purposes and the desired properties; as a result of its rather low solubility in water or body fluids this active substance is released only very slowly and therefore develops its bactericidal effect for as long as 3 to 4 weeks. Vasoactive and pH-regulating substances may also be used. When the container according to the invention, i.g. a dialysis tube containing the pharmaceutical active substance, is used in wounds and wound cavities, increased exudation is also found, which promotes the desired effect even further. If, on the other hand, the active substances, e.g. taurolidine, is introduced directly into the wound in dissolved form, after 3 to 4 hours it has all been washed out again, precisely because of this increased exudation, and its activity it thus rapidly terminated.

One advantage of the device according to the invention is that it avoids local high concentrations of the active substance in contact with body tissues. In the case of taurolidine, 2% solutions have been known to give painful tissue reactions in some open wounds. A device according to the invention comprising particulate taurolidine contained in a dialysis tube permits concentrations of taurolidine to build up to levels of the order of 0.5% which do not give a painful reaction, while being quite adequate to kill any pathogens present, even difficult phatogens such as Pseudomonas species.

The device according to the invention may contain a solid or liquid pharmaceutically active substance; a solid active substance is preferably present in finely divided form, more particularly powdered, but depending on the membrane used it may also be used in solution, particularly in a physiologically compatible organic solvent which is difficultly soluble in water or only partly water-miscible.

The contents of the device according to the invention may also be precursors of the active subtances (e.g. complexes, non-dialysible complexes, polymers) from which the actual dialysable active substance is formed by enzymatic or chemical reaction. The term "precursors" of the active substance for the purposes of the invention also refers to living cells, of human or other origin, preferably cells of connective tissue or bone which are able to release active substances to the surrounding medium.

Examples of such cells forming such a precursor included: histiocytes, plasma cells, mast cells, eosinophilic cells, pigment cells, white blood cells, the parent cells of white and red blood cells, cartilage cells including the formative and degraded forms, bone cells including the formative and degraded forms and fat cells. An advantage of this embodiment of the invention is the fact that the membrane, particularly when a semipermeable membrane, protects the living cells from the body's immune system but allows the active substances, e.g. interleukins, to be released into the environment. This gives rise to new possible methods of treating diseases of the immune system, for healing bone fractures and the like.

The function of the membrane is to retain the main body of the active substance or precursor while releasing the active substance over a prolonged period. Where the active substance is a solid particulate material it may be sufficient for the membrane to possess pores (or other means permitting release of the substance) which are small enough to retain the particles within but do not restrict ingress of body fluids. By simply retaining the particulate active material, release into the external bady fluids is limited largely by water solubility and commonly achieves a desired zero-order release rate. Where, however, it is desired to protect the main body of the active material, from components of the body fluids, notably enzymes, the membrane is desirably a semipermeable membrane, for example with a cut-off in the region 50,000 Daltons. In general, semipermeable membranes provide a useful, relatively slow, release rate even where there is no need to prevent ingress of enzymes and are generally preferred.

The walls of the container according to the invention may consist wholly or partly of the said membrane, the container may be, for example, a plastics container consisting of a physiologically well-tolerated, sufficiently flexible plastics, e.g. a plastics tube, plastics sack or a preferably readily deformable plastics sphere which has one or more windows consisting of the said membrane; however, the container preferably consists of one or more tubes or hollow fibres consisting of a semi-permeable membrane and is in particular a dialysis tube, of the type which is commercially available. The use of a slightly flexible tube has the particular advantage that it can easily be inserted in the wound and removed again, it can fit the special shape of the wound or wound cavity, and if necessary, can be coiled. Instead of a single tube it is also possible to use a bundle of hollow fibres containing the pharmaceutically active substance. Suitable plastics for the containers according to the invention include all the physiologically acceptable plastics which are suitable for implants (cf. for example Angewandte chemie 82, (1970) 367–379; 86I (1974) 145–150).

Semi-permeable membranes which may be used according to the invention may be natural and preferable artificial (semi-synthetic or synthetic) hydrophilic or hydrophobic membranes; all membranes which are used for artificial kidneys are particularly suitable; the membranes are preferably used in the form of hollow fibres and particularly tubes. Natural membranes include, for example, pigs bladders, fishes' swim bladders and intestines; artifically produced membranes are preferable those based on cellulose or cellulose derivatives such as, for example, regenerated cellulose (cellophane), parchment paper, collodion skins, cellulose acetate; or those based entirely on synthetic substances, e.g. polyethylene, polystyrene, polyacrylonitrile, polyacrylnitrilecopolymers, N-methylpyrrolidone, coated onto polyethylene film, copolyetheresters such as polyethylene glycol/polyethylene terephthalate or silicones. The advantages of hydrophobic membranes such as silicone membranes include, in addition to their good compatibility with the tissue, their permeablity to hydrophobic active substances such as corticosteroids. In the case of an aqueous cortisone solution, for example, such membranes prevent the water from passing through but not the cortisone, Hydrophilic membranes are suitable for hydrophilic active substances and let water through. Therefore, non-dissolved active substances may be used, which dissolve in the penetrating water of the tissues and diffuse out.

Preferably, the compatibility of the membranes with the blood is futher improved by a known surface modification, such as membrane heparinisation; thus, ethyleneimine may be coated onto cellulose membranes and then used to bind heparin, or cellulose acetate, e.g. cellulose acetate tubes or hollow fibres, may be deacylated with hydroxlyamine, after which the heparin is bonded via bromocyanogen (cf. Hasenfratz and G. Knaup, Artificial Organs, Vol. 5. (Suppl.) 1981, 507–511). The layer thicknesses of the semi-permeable membranes which may be used according to the invention preferably range from 10 to 110 um. The thickness of the tubes and the legth of the tubes or bundle of hollow fibres is not critical and is determined particularly by the intended application (nature, form and size of the wound or wound cavity, etc) and also by the nature of the wall material; the thickness of the tube is generaly from 0.3 to 2 cm.

In a particularly convenient embodiment of the apparatus according to the invention the container, e.g. dialysis tube, containing the pharmaceutically active substance is functionally combined with a tubular drainage device for draining wound secretions out of wounds or wound cavities. This combines the function of the device containg pharmaceutically active substance according to the invention (controlled release of the active substance over a fairly long periord of time) with the function of the drainage device (draining off wound secretions and avoiding accumulations of secretions in wound cavities).

The drainage device may, theoretically, be any tubular drainage device conventionally used in surgery. Suction drainage tubes in which secretions are conveyed through the drainage tube under reduced pressure (less than atmospheric pressure) are particularly suitable. In addition to the better and safer discharge of the wound secretions, a further advantage of suction drainage tubes is that the wound cavities are reduced in size by the application of suction, provided that the resilient recoil forces of the tissues permit, thus more easily achieving the contact between the walls of the wound cavity required for healing.

The drainage tubes may consist of a physiologically compatible material conventionally used for such purposes, e.g. made of rubber or more preferably, plastics. The plastics material may be any physiologically acceptable plastics material conventionally used for these purposes (cf. Angewandte chemie 82, (1970) 367–379; 86I (1974) 145–150). The diameter and length of the drainage tubes depend on the intended purpose; the diameter is generally of the order of 0.5 cm. Preferably, the so called Redon drainage tube is used as the tubular drainage device, whilst a vacuum suction drainage tube is preferably used for festering wounds.

The drainage tube consists of a fairly rigid PVC tube about 0.5 cm in diameter and up to 1 m long, to which reduced pressure is applied.

For functionally combining the container containing the pharmaceutically active substance to the drainage device, one or more containers, preferably one or more semi-permeable membrane tubes, may be connected to the end of the drainage device leading into the wound, e.g. with surgical sutures or by knotting the membrane tube; however, it is also possible for the container and drainage tube to be placed in the wound cavity separately but adjacent each other so that the drainage device performs the function of draining the secretions. A fixed connection between a tubular container according to the invention and the drainage tube has the advantage that both tubes can be pulled out of the wound together. In a preferred embodiment, the tube is a drainage device which contains over its entire length or part thereof, a semi-permeable membrane tube, e.g. a dialysis tube, which extends inside the tubular drainage device and projects out of the end inserted in the body to a suitable length for the intended purpose (size of the wound cavity) and extends into the wound cavity; the diameter of the drainage tube and dialysis tube should differ sufficiently to ensure that the secretions are properly drained off. In this embodiment the dialysis tube may be pulled out of the wound through the drainage tube or together with the latter.

In a particularly preferred embodiment, the tubular drainage device, particularly if it operates at reduced pressure, is constructed so that the end of the tube located in the body, i.e. against the wound, is split into several filaments ("frayed" rather like a horses tail or cauda drainage device) between which the liquid to be discharged can trickle in. The filaments may be formed as strips (e.g. by cutting into the end of the tube) or as fibres and by arranged side by side in a flat arrangement or in a bundle. The number of filaments is not critical; it is generally from 4 to 20, particularly from 8 to 12. The length of the filaments depends particularly on the envisaged use (e.g. the size of the wound cavity; it is generally between 5 and 20 cm.

In known improved embodiments of tubular drainage devices, such as Redon tube, the end portion, i.e. the part of the tube adjacent to the wound, is provided with perforations which become larger and larger towards the end of the tube in order to improve the discharge of secretions; in another embodiment the drainage tube is provided with a spirally progressing groove. However, these drainage tubes have the disadvantage that they can only be pulled out of the wound by overcoming some resistance, particularly if suction is used, which will be painful for the patient. Moreover, the shape edged perforations or grooves may cause some tearing of tissue or coagulated blood when pulled out, thus causing fresh bleeding. These disadvantages can be avoided with the preferred embodiment of the drainage device according to the invention in which the section of tube located in the body ends in a plurality of filaments. These drainage tubes can be removed from the wound without any difficulty, with no pain, and no fresh bleeding.

The containers according to the invention, particularly membrane tubes, may be combined with the drainage tubes preferred according to the invention in the manner described above, e.g. by securing dialysis tubes at the end of the drainage tube or by passing a dialysis tube through the drainage tube; however, it is advantageous to split the end into filaments because this enables the dialysis tubes to be fixed easily to the filaments, e.g. by knotting or by covering one or more filaments with the dialysis tubes, whilst maintaining the full draining effect.

The present invention therefore also relates to a tubular drainage device which is particularly suitable for combining a container according to the invention having semi-permeable walls and containing a pharmaceutically active substance, this drainage device being characterised in that its end located in the body, i.e. at the wound, is split into several filaments, i.e. terminates in a plurality of filaments (cauda drainage).

FIG. 1 shows, by way of example, a device according to the invention consisting of drainage tube and dialysis tube, without restricting the invention thereto;

A drainage tube (1) has filaments (2) at its end which is inserted into the wound. Emerging from the end of the drainage tube is a dialysis tube (3) which is inserted in the wound; in the section of dialysis tube which is located in the wound there is a powdered pharmaceutically active substance, e.g. taurolidine (4); to retain the active substance, the dialysis tube is knotted or constricted (5).

I claim:

1. A device for inserting in wounds and wound cavities, comprising a container containing a pharmaceutically active solid substance, said container having walls formed, at least partially, of a membrane which allows the active substance to escape into the wound area, said pharmaceutically active substance having a low water solubility and being in the form of particles, said membrane comprising pores which are small enough to retain the particles within but do not restrict ingress of external body fluids, wherein the release rate of the substance into the external body fluids is limited largely by said water solubility; and a tubular wound drainage device connected to said container for draining away wound secretions from wounds and wound cavities wherein the tubular wound drainage device has an end for insertion in the body and said end is split into several filaments to facilitate wound drainage.

2. The device of claim 1 in which the membrane is a semipermeable membrane.

3. The device of claim 2, wherein the container is a tube formed of the semi-permeable membrane.

4. The device of claim 3, wherein the container is a dialysis tube.

5. The device of claim 1 wherein the pharmaceutically active substance is in powder form.

6. The device of claim 1 wherein the pharmaceutically active substance is a substance with anti-bacterial and/or antitoxic activity.

7. The device of claim 1 wherein the pharmaceutically active substance is taurolidine.

8. The device of claim 1 wherein the container comprises a bundle of hollow fibers.

9. A method of treatment of wounds and wound cavities wherein a device as claimed in claim 1 is inserted in said wound.

10. The method of claim 9 wherein the wounds to be treated are osteitis or osteomyelitis cavities.

11. The device of claim 1 wherein the release of the substance into the external body fluids achieves a zero-order release rate.

12. A device for inserting in wounds and wound cavities, comprising a container containing a solid precursor being able to form a pharmaceutically active substance by a chemical or enzymatic reaction, said container having walls formed, at least partially, of a membrane which allows said pharmaceutically active substance and/or said precursor to escape into the wound area, said precursor having a low water solubility and being in the form of particles, said membrane comprising pores which are small enough to retain the particles within but do not restrict ingress of external body fluids, wherein the release of the pharmaceutically active substance and/or said precursor into the external body fluids is limited largely by water solubility; and a tubular wound drainage device connected to said container for draining away wound secretions from wounds and wound cavities wherein the tubular wound drainage device has an end for insertion in the body and said end is split into several filaments to facilitate wound drainage.

13. The device of claim 12 wherein the precursor comprises living cells of connective tissue.

14. The device of claim 12 wherein the release of the substance and/or precursor into the external body fluids achieves a zero-order release rate.

* * * * *

UNITED STATES PATENT AND TRADEMARK OFFICE
CERTIFICATE OF CORRECTION

PATENT NO. : 4,960,415
DATED : October 2, 1990
INVENTOR(S) : Johannes Reinmüller It is certified that error appears in the above-identified patent and that said Letters Patent is hereby corrected as shown below:

Column 1, line 5, "878,848" should read --878,842--.

Column 1, line 11, "threat" should read --treat--.

Column 1, line 34, "exotosins" should read --exotoxins--.

Column 2, line 29, "i.g." should read --e.g.--.

Column 3, line 24, "bady" should read --body--.

Column 4, line 29, "legth" should read --length--.

Signed and Sealed this

Fourth Day of August, 1992

Attest:

DOUGLAS B. COMER

Attesting Officer

Acting Commissioner of Patents and Trademarks